United States Patent
Yoshioka et al.

(10) Patent No.: US 10,942,965 B2
(45) Date of Patent: *Mar. 9, 2021

(54) INFORMATION PROCESSING APPARATUS AND INFORMATION PROCESSING METHOD

(71) Applicant: SONY CORPORATION, Tokyo (JP)

(72) Inventors: Shigeatsu Yoshioka, Kanagawa (JP); Masahiro Takahashi, Kanagawa (JP); Hiroshi Yamaguchi, Tokyo (JP); Masayuki Morota, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/701,596

(22) Filed: Sep. 12, 2017

(65) Prior Publication Data
US 2018/0004774 A1    Jan. 4, 2018

Related U.S. Application Data

(63) Continuation of application No. 13/875,946, filed on May 2, 2013, now Pat. No. 9,792,302.

(30) Foreign Application Priority Data

May 14, 2012 (JP) .............................. JP2012-110999

(51) Int. Cl.
*G06F 17/00* (2019.01)
*G06F 16/58* (2019.01)
(Continued)

(52) U.S. Cl.
CPC ............. *G06F 16/58* (2019.01); *G06F 19/00* (2013.01); *G06F 19/321* (2013.01); *G16H 40/63* (2018.01); *G16H 50/20* (2018.01)

(58) Field of Classification Search
CPC ............. G06F 17/30265; G06F 19/321; G06F 19/3406; G06F 19/345; G06F 19/327;
(Continued)

(56) References Cited

U.S. PATENT DOCUMENTS 6,272,235 B1 * 8/2001 Bacus ................ G01N 15/1475
382/133
7,296,016 B1 * 11/2007 Farach-Colton .... G06F 16/9535
(Continued)

FOREIGN PATENT DOCUMENTS

JP    2012-065271 A    3/2012

OTHER PUBLICATIONS

Notice of Allowance and Fees Due for U.S. Appl. No. 13/875,946, dated Jun. 16, 2017, 17 pages.
(Continued)

*Primary Examiner* — Hasanul Mobin
(74) *Attorney, Agent, or Firm* — Chip Law Group

(57) ABSTRACT

A pathological image and a primary diagnosis result are obtained from a first terminal via a network, the first terminal being of a first user, the primary diagnosis result being a diagnosis result about the pathological image by the first user. The obtained pathological image and the primary diagnosis result are provided to at least one second terminal via the network, the one second terminal being of at least one second user. A browsing history and an opinion of the second user are obtained from the second terminal via the network, the browsing history at least including information on a displayed area in the pathological image, the opinion of the second user being about the primary diagnosis result based on observation of the pathological image by the second user. The obtained browsing history is estimated, and a reliability score of the obtained opinion is generated.

12 Claims, 12 Drawing Sheets

(51) Int. Cl.
  *G06F 19/00*  (2018.01)
  *G16H 40/63*  (2018.01)
  *G16H 50/20*  (2018.01)

(58) Field of Classification Search
  CPC ...... G06F 16/5838; G06F 16/58; G06F 19/00; G06H 40/63
  See application file for complete search history.

(56) References Cited

U.S. PATENT DOCUMENTS

| | | | |
|---|---|---|---|
| 2002/0073429 A1* | 6/2002 | Beane | G06F 19/321 725/105 |
| 2003/0063300 A1* | 4/2003 | Rubinstenn | G06F 19/00 358/1.9 |
| 2003/0065636 A1* | 4/2003 | Peyrelevade | G06Q 30/0601 706/62 |
| 2003/0163031 A1 | 8/2003 | Madden et al. | |
| 2003/0177041 A1* | 9/2003 | Millican, III | G06Q 50/24 705/3 |
| 2004/0019501 A1* | 1/2004 | White | G16H 40/20 705/2 |
| 2005/0110788 A1 | 5/2005 | Turner et al. | |
| 2005/0216581 A1* | 9/2005 | Blumenau | H04L 67/02 709/223 |
| 2005/0240882 A1 | 10/2005 | Morita et al. | |
| 2007/0127793 A1* | 6/2007 | Beckett | G06T 7/0012 382/128 |
| 2007/0237377 A1* | 10/2007 | Oosawa | G06F 19/321 382/128 |
| 2007/0282825 A1 | 12/2007 | Toub | |
| 2008/0260226 A1* | 10/2008 | Moriya | G06K 9/6201 382/128 |
| 2009/0119258 A1* | 5/2009 | Petty | G06Q 10/10 |
| 2009/0292814 A1 | 11/2009 | Ting et al. | |
| 2009/0319273 A1* | 12/2009 | Mitsui | G06F 17/30053 704/260 |
| 2010/0083144 A1 | 4/2010 | Baxley et al. | |
| 2011/0022658 A1* | 1/2011 | Pace | G06Q 10/10 709/204 |
| 2011/0191696 A1* | 8/2011 | Jain | G06F 3/00 715/758 |
| 2011/0238402 A1* | 9/2011 | Kotani | H04L 9/0897 703/22 |
| 2011/0239243 A1* | 9/2011 | Dierks | H04H 60/33 725/14 |
| 2011/0295689 A1* | 12/2011 | Brady | G06Q 30/0241 705/14.54 |
| 2012/0124487 A1* | 5/2012 | Edgar | G06Q 10/10 715/760 |
| 2013/0054675 A1* | 2/2013 | Jenkins | H04L 67/02 709/203 |
| 2013/0080071 A1* | 3/2013 | Holmes | G16H 10/40 702/21 |
| 2014/0033007 A1* | 1/2014 | Mhatre | G06F 17/214 715/205 |

OTHER PUBLICATIONS

Advisory Action for U.S. Appl. No. 13/875,946, dated Mar. 21, 2017, 03 pages.
Final Rejection for U.S. Appl. No. 13/875,946, dated Dec. 29, 2016, 16 pages.
Non-Final Rejection for U.S. Appl. No. 13/875,946, dated Jun. 15, 2016, 15 pages.
Final Rejection for U.S. Appl. No. 13/875,946, dated Dec. 21, 2015, 15 pages.
Non-Final Rejection for U.S. Appl. No. 13/875,946, dated Jun. 18, 2015, 15 pages.

* cited by examiner

People, who double check the following pathological diagnosis, are wanted.   Pathologist name: OOOO
(Pathologist No.: XXXX)

31 January 2012

Clinical diagnosis: left breast cancer, resect outer part
Histopathological diagnosis:
1. Breast, left, partial resection (#1-30) —
2. INVASIVE DUCTAL CARCINOMA (#5-9)
   (a) SCIRRHOUS, grade 2, size: 2 x 2 x 1 cm, CD region,
   (b) intraductal spreading ++, surgical margins: negative.
   (c) f -, ly +, v -, s -
   (d) T1n1mX (stage I, when m0)
   (e) ER +, PgR +, p53 -, HER-2 (c-erb B2) 1+, MIB-1 20%
3. MASTOPATHY
   (a) (intraductal papillomatosis, adenosis, apocrine metaplasia)
4. Lymph nodes, axilla, dissection —
5. METASTATIC DUCTAL CARCINOMA, n 1/14
   (a) n(SN) 1/2, n level I 0/9, n level II 0/3

Remarks:
A) A partial resected material (9x6 cm) of a mammary gland is obtained. A skin is attached to a part of the partial resected material. The primary focus (grayish white, scirrhus, 2x2x1 cm) is prepared from the partial resected material. 30 blocks, in total, at about 5 mm intervals are prepared from the partial resected material, the resection stump being the center. The primary focus and the 30 blocks are observed.
B) From a histological point of view, relatively small cancer cells propagate in a small restiform configuration or in an alveolar configuration. The cancer cells make invasion in adipose tissues ununiformly (sample #5-9). Interstitial fibrosis is also observed. The interstitial fibrosis is distinct in the center portion of the lesion. Anisokaryosis is low. However, chromatin is relatively increased. It is determined that the degree of nuclear atypia is grade 2. A few mitosis is detected. It is confirmed that tubular structures are partially formed. The diagnosis is ductal breast cancer of degree of malignancy (grade) 2. Slight lymphocytic invasion is found around the tumor cell nest. Slight lymphovascular invasion is found. Vein invasion is not found. No skin invasion.

INFORMATION PROCESSING APPARATUS AND INFORMATION PROCESSING METHOD

CROSS REFERENCES TO RELATED APPLICATIONS

The present application is a continuation application of U.S. patent application Ser. No. 13/875,946, filed May 2, 2013, and claims the priority from prior Japanese Patent Application JP 2012-110999 filed in the Japan Patent Office on May 14, 2012. Each of the above-referenced applications is hereby incorporated herein by reference in its entirety.

BACKGROUND

The present disclosure relates to an information processing apparatus, an information processing method, and an information processing program, each of which uses a pathologist-dedicated SNS (Social Network Service).

Recently, various SNSs are provided. Many comments are posted on SNS. It is desirable to filter writers, who posted comments, based on a specific index, to narrow down comments to read, and to thus reduce labor to read comments.

For example, Japanese Patent Application Laid-open No. 2012-065271 discloses an example of such an index. According to the technology of Japanese Patent Application Laid-open No. 2012-065271, an index, i.e., contact frequency with contacts in an address book, is calculated for each of a plurality of mobile terminals. The calculated index is used.

SUMMARY

The number of pathologists in a hospital is limited. In this situation, it is desirable to post a primary diagnosis by a comment-seeker by using an SNS, and to collect comments from applicants. The comments are double checks or second opinions about the posted primary diagnosis. As a result, it is desirable to increase a double check rate of a virtual slide sample, and to improve diagnosis accuracy.

However, since this is pathological diagnosis, extremely high reliability is required for posting. When applicants state their opinions about primary diagnosis by a seeker, some applicants may only show their approval. In view of this, it happens that reliability becomes a problem. Here, reliability means if a comment is as the result of diagnosis executed by an applicant, or not. It is difficult to improve reliability of a posted comment, only by reading what is stated in the posted comment.

In view of the above-mentioned circumstances, it is desirable to provide an information processing apparatus, an information processing method, and an information processing program capable of improving reliability of comments posted on a pathologist-dedicated SNS.

(1) According to an embodiment of the present technology, there is provided an information processing apparatus, including: a first information obtaining section configured to obtain a pathological image and a primary diagnosis result from a first terminal via a network, the first terminal being of a first user being a pathologist, the primary diagnosis result being a diagnosis result about the pathological image by the first user; an information providing section configured to provide the obtained pathological image and the primary diagnosis result to at least one second terminal via the network, the at least one second terminal being of at least one second user being a pathologist; a second information obtaining section configured to obtain a browsing history and an opinion of the second user from the second terminal via the network, the browsing history at least including information on a displayed area in the pathological image, the area being displayed based on operation by the second user when the second user observes the pathological image on a display unit of the second terminal, the opinion of the second user being about the primary diagnosis result based on observation of the pathological image by the second user; and a reliability score generating section configured to estimate the obtained browsing history based on a predetermined condition, and to generate a reliability score of the obtained opinion.

The present technology relates to an SNS, of which users are pathologists. The information processing apparatus of the present technology functions as a server computer. The first user is a seeker, who wants double checks and second opinions about his diagnosis. The first user uploads pathological images and a primary diagnosis result on an SNS via the first information obtaining section. The primary diagnosis result is a diagnosis result by the first user. The first user collects opinions (posted comments). The second user is an applicant candidate as well as an applicant. The second user watches the pathological image and reads the primary diagnosis result by means of the information providing section. The pathological image and the primary diagnosis result are uploaded on the SNS. After that, the second user uploads, i.e., submits, his opinion (posted comment) via the second information obtaining section on the SNS. When the second user browses the pathological image displayed on the display unit of the second terminal, information on an area displayed on the display unit is recorded. The information processing apparatus obtains the recorded information on the displayed area by means of the second information obtaining section. How the second user observes the target pathological image in detail is determined. As a result, it is possible to determine reliability of an opinion (posted comment) of the second user. In view of this, a condition when the second user browses a pathological image is preset, and a score corresponding to the condition is preset. How browsing behavior of the second user conforms to the condition is determined. A reliability score is generated based on that. As a result, it is possible to easily generate a reliability score of a comment posted on the pathologist-dedicated SNS, which is effective.

(2) Further, in the information processing apparatus according to an embodiment of the present technology, the second information obtaining section is configured to obtain, as the browsing history, information at least including information of a browsing time period of the pathological image, and the reliability score generating section is configured to generate a reliability score of the obtained opinion based on at least the obtained browsing time period.

According to the present technology, a browsing time period of a pathological image is used as an index of determining how the second user watches the pathological image in detail, i.e., reliability of an opinion. If a browsing time period is too short, reliability of an opinion based on the browsing may be low. If a browsing time period is used as an index, it is possible to generate a reliability score of a comment posted on the pathologist-dedicated SNS more appropriately, which is effective.

(3) Further, in the information processing apparatus according to an embodiment of the present technology, the second information obtaining section is configured to obtain, as the browsing history, information at least including information on observation magnification of the pathological image, and the reliability score generating section is configured to generate a reliability score of the obtained opinion based on at least the obtained observation magnification.

According to the present technology, observation magnification of a pathological image is used as an index of determining how the second user watches the pathological image in detail, i.e., reliability of an opinion. Reliability of an opinion based on browsing with higher observation magnification may be higher than reliability of an opinion based on browsing with lower observation magnification. If observation magnification is used as an index, it is possible to generate a reliability score of a comment posted on the pathologist-dedicated SNS more appropriately, which is effective.

(4) Further, in the information processing apparatus according to an embodiment of the present technology, the second information obtaining section is configured to obtain, as the browsing history, information at least including information on a browsed area in the pathological image, and the reliability score generating section is configured to generate a reliability score of the obtained opinion based on at least the obtained browsed area.

According to the present technology, information on a browsed area in a pathological image is used as an index of determining how the second user watches the pathological image in detail, i.e., reliability of an opinion. For example, reliability of an opinion, which is written by browsing the entire area of a sample, is higher than reliability of an opinion, which is written by browsing a part of the sample, because of less oversight. If a browsed area is used as an index, it is possible to generate a reliability score of a comment posted on the pathologist-dedicated SNS more appropriately, which is effective.

(5) Further, in the information processing apparatus according to an embodiment of the present technology, the second information obtaining section is configured to obtain information showing a noteworthy position in the pathological image, and the reliability score generating section is configured to generate a reliability score of the obtained opinion based on at least presence/absence of the obtained noteworthy position.

According to the present technology, information on if a noteworthy position is set in a pathological image or not is used as an index of determining how the second user watches the pathological image in detail, i.e., reliability of an opinion. The second user may show a noteworthy position in a pathological image to corroborate his opinion. That is, a reliability score of an opinion with a set noteworthy position may be higher than a reliability score of an opinion without a noteworthy position. As a result, if presence/absence of a set noteworthy position is used as an index, it is possible to generate a reliability score of a comment posted on the pathologist-dedicated SNS more appropriately, which is effective.

(6) Further, the information processing apparatus according to an embodiment of the present technology further includes: a first browsing history obtaining section configured to obtain, as a first browsing history, a browsing history from the first terminal of the first user, the browsing history at least including information on a displayed area in the pathological image, the area being displayed based on operation by the first user when the first user observes the pathological image on a display unit of the first terminal; a browsing history mixing section configured to mix at least one browsing history of at least one second user to obtain one browsing history being a mixed browsing history, the at least one browsing history being obtained by the second information obtaining section; and a browsing history difference generating section configured to generate difference between the mixed browsing history obtained by the browsing history mixing section and the first browsing history obtained by the first browsing history obtaining section.

According to the present technology, first, the first browsing history obtaining section obtains, as the first browsing history, a browsing history when the first user browses a pathological image for primary diagnosis. Next, the browsing history mixing section mixes all the browsing histories of a plurality of second users, to thereby generate a mixed browsing history. The mixed browsing history shows all the areas, which are browsed by at least one second user out of all the second users, in the pathological image. Next, the browsing history difference generating section obtains the difference between the first browsing history and the mixed browsing history. The difference between areas, which are browsed by a first user who executes the primary diagnosis, and areas, which are browsed by other users, may be apparent from the difference. As a result, the first user is capable of finding areas, to which other users have paid attention, and which the seeker has not found, which is effective.

(7) Further, According to another embodiment of the present technology, there is provided an information processing method, including: obtaining, by a first information obtaining section, a pathological image and a primary diagnosis result from a first terminal via a network, the first terminal being of a first user being a pathologist, the primary diagnosis result being a diagnosis result about the pathological image by the first user; providing, by an information providing section, the obtained pathological image and the primary diagnosis result to at least one second terminal via the network, the at least one second terminal being of at least one second user being a pathologist; obtaining, by a second information obtaining section, a browsing history and an opinion of the second user from the second terminal via the network, the browsing history at least including information on a displayed area in the pathological image, the area being displayed based on operation by the second user when the second user observes the pathological image on a display unit of the second terminal, the opinion of the second user being about the primary diagnosis result based on observation of the pathological image by the second user; and estimating, by a reliability score generating section, the obtained browsing history based on a predetermined condition, and generating a reliability score of the obtained opinion.

(8) Further, According to another embodiment of the present technology, there is provided an information processing program, causing a computer to function as: a first information obtaining section configured to obtain a pathological image and a primary diagnosis result from a first terminal via a network, the first terminal being of a first user being a pathologist, the primary diagnosis result being a diagnosis result about the pathological image by the first user; an information providing section configured to provide the obtained pathological image and the primary diagnosis result to at least one second terminal via the network, the at least one second terminal being of at least one second user being a pathologist; a second information obtaining section configured to obtain a browsing history and an opinion of the second user from the second terminal via the network, the browsing history at least including information on a displayed area in the pathological image, the area being displayed based on operation by the second user when the second user observes the pathological image on a display unit of the second terminal, the opinion of the second user being about the primary diagnosis result based on observation of the pathological image by the second user; and a reliability score generating section configured to estimate the obtained browsing history based on a predetermined condition, and to generate a reliability score of the obtained opinion.

As described above, according to the present technology, it is possible to easily generate a reliability score of a comment posted on the pathologist-dedicated SNS.

These and other objects, features and advantages of the present disclosure will become more apparent in light of the following detailed description of best mode embodiments thereof, as illustrated in the accompanying drawings.

BRIEF DESCRIPTION OF DRAWINGS

FIG. 9 is an example of an article for collecting comments, which is displayed on an SNS window of an applicant candidate;

FIG. 10 is an example of a diagnosis report window (submission window), which is posted by an applicant;

DETAILED DESCRIPTION OF EMBODIMENTS

Hereinafter, an embodiment of the present disclosure will be described with reference to the drawings.

First Embodiment

[Configuration of Pathologist-Dedicated SNS System]

First, an overview of a pathologist-dedicated SNS system will be described.

Figure 1:
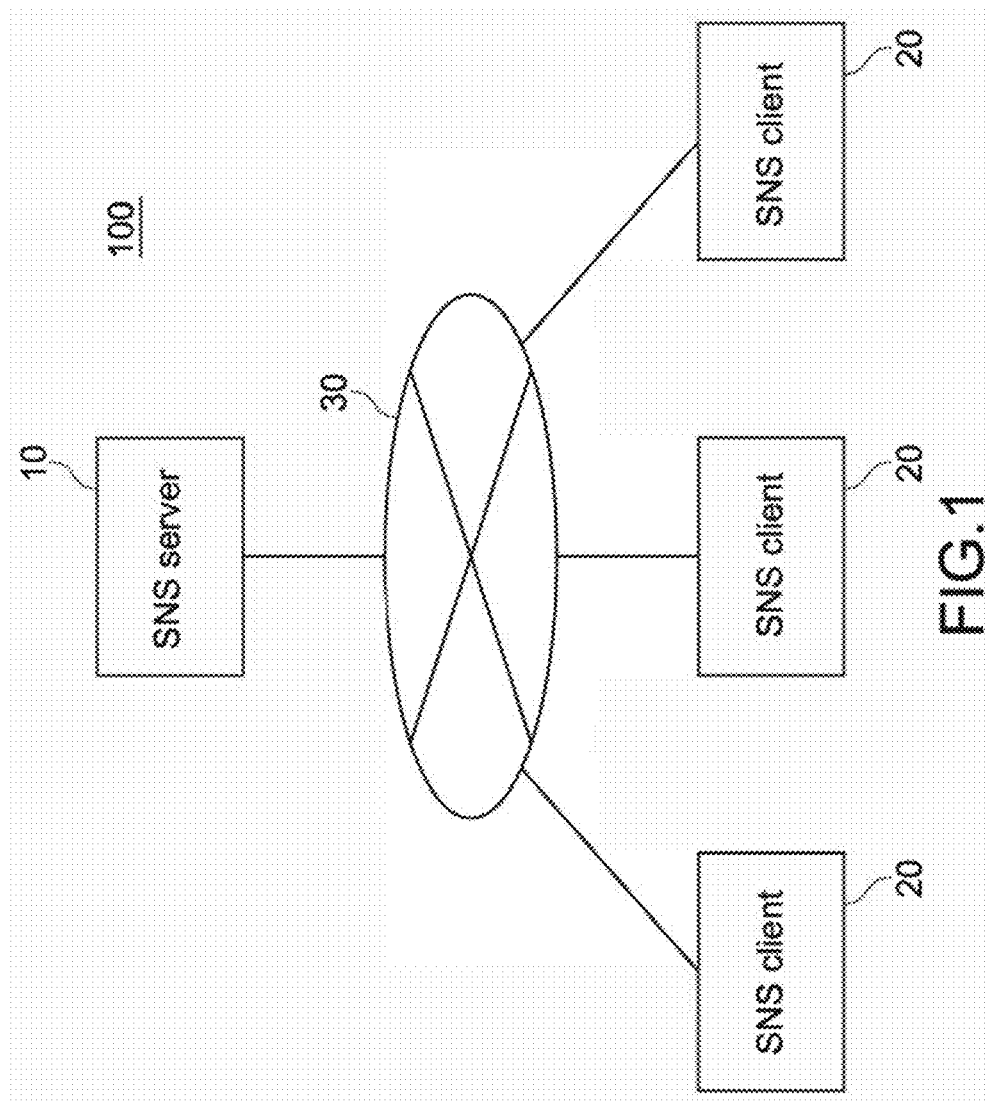
FIG. 1 is a diagram schematically showing the configuration of a first embodiment of the present technology.

FIG. 1 is a schematic diagram showing the configuration of a first embodiment of the present technology. A pathologist-dedicated SNS system 100 includes an SNS server 10, SNS clients 20, and a network 30. Note that although FIG. 1 shows the three SNS clients, the pathologist-dedicated SNS system 100 may include at least one SNS client.

The SNS server 10 may be a general-purpose computer. The SNS client 20 may be a general-purpose computer.

An example of the network 30 is the Internet. However, the network 30 may be a network employing dedicated lines or a network in the Internet employing a VPN (Virtual Private Network), because pathological diagnosis images and detailed diagnosis flow in the pathologist-dedicated SNS system 100.

The pathologist-dedicated SNS system 100 may be operated as a part of an LIS (Laboratory Information System).

[Hardware Configuration of Each of SNS Server 10 and SNS Client 20]

Next, the configuration of each of the SNS server 10 and the SNS client 20 will be described. A general-purpose computer is used as the SNS server 10 or the SNS client 20. The configuration of the SNS server 10 is basically the same as the configuration of the SNS client 20. So the configuration of the SNS server 10 will only be described.

Figure 2:
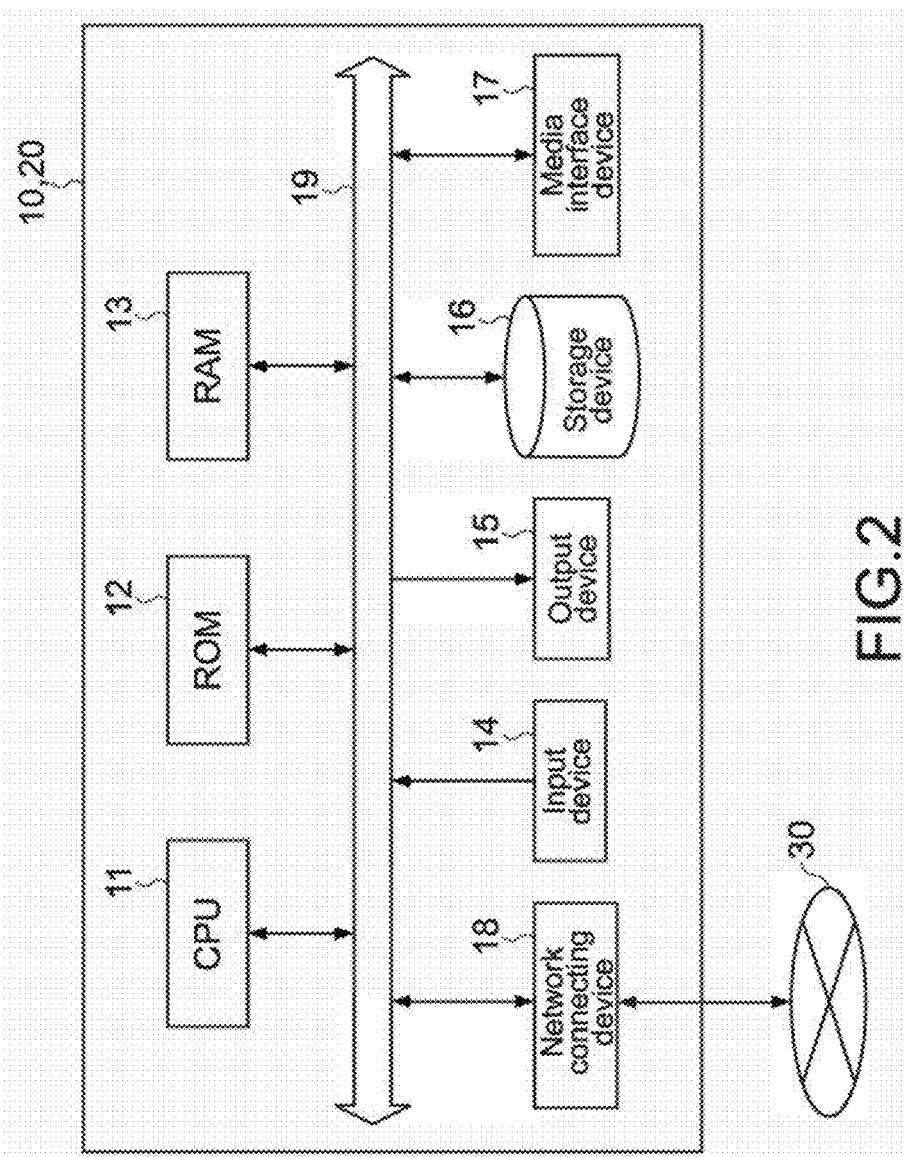
FIG. 2 is a diagram showing the hardware configuration of an SNS server 10.

FIG. 2 is a diagram showing the hardware configuration of the SNS server 10.

As shown in FIG. 2, the SNS server 10 includes a CPU (Central Processing Unit) 11, a ROM (Read Only Memory) 12, and a RAM (Random Access Memory) 13. Further, the SNS server 10 includes an input device 14, an output device 15, a storage device 16, a media interface device 17, a network connecting device 18, and a bus 19 connecting them.

The CPU 11 functions as an arithmetic processing unit and a control unit. Various programs cause the CPU 11 to control overall behavior of the SNS server 10. The ROM 12 stores the programs, arithmetic parameters, and the like used by the CPU 11. The RAM 13 temporarily stores a program executed by the CPU 11, parameters which are changed arbitrarily during execution of the program, and the like.

An image control section 101, an SNS control section 103, and the like (described later) of the SNS server 10 are realized by, for example, the CPU 11, programs stored in the ROM 12, the work area of the RAM 13, and the like in the hardware configuration of the SNS server 10. An SNS client control section 201 and a viewer control section 202 of the SNS client 20 are realized by the CPU 11, programs stored in the ROM 12, the work area of the RAM 13, and the like.

The input device 14 includes an input means, in which a user inputs information. Examples of the input means include a mouse, a keyboard, a touchscreen, a button, a microphone, a switch, a lever, and the like. The input device 14 further includes, for example, an input control circuit configured to generate an input signal based on input by a user, and to output the input signal to the CPU 11.

The output device 15 includes a display device such as, for example, a CRT (Cathode Ray Tube) display device, a liquid crystal display (LCD) device, an OLED (Organic Light Emitting Diode) device, or the like. Further, the output device 15 includes a sound output device such as a speaker or a headphone.

The storage device 16 stores programs and user data. The storage device 16 includes a storage medium, a reader/writer device configured to read/write data from/in the storage medium, and the like. The storage device 16 includes, for example, an HDD (Hard Disk Drive), an SSD (Solid State Drive), or the like.

The media interface device 17 is a reader/writer for a storage medium. The media interface device 17 reads/writes data from/in a mounted removal storage medium such as a magnetic disk, an optical disk, a magnet-optical disk, or a semiconductor memory.

The network connecting device 18 is, for example, configured to connect the network 30. The network connecting device 18 may be a device for a wireless LAN (Local Area Network), a device for a wireless USB, or a communication device performing wired communication.

[Functional Block of SNS Server 10]

Figure 3:
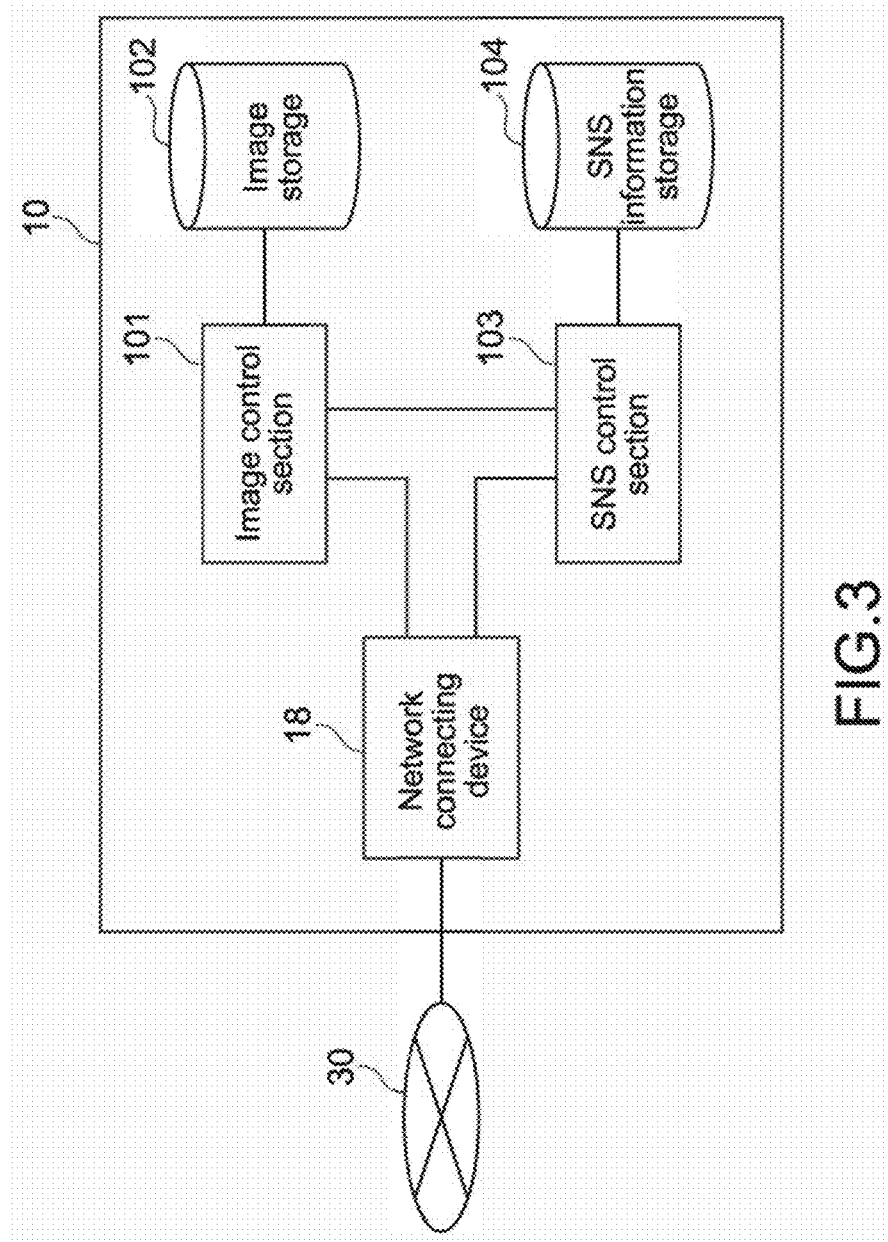
FIG. 3 is a diagram showing the functional blocks of the SNS server 10.

FIG. 3 shows the functional blocks of the SNS server 10. The SNS server 10 includes the image control section 101 (first information obtaining section), an image storage 102, the SNS control section 103 (first information obtaining section, information providing section, second information obtaining section, reliability score generating section), an SNS information storage 104, and the above-mentioned network connecting device 18.

The image storage 102 stores virtual slide images (pathological images) for pathological diagnosis. The image storage 102 stores virtual slide images. A seeker, who wants comments as double checks and second opinions in an SNS, posts the virtual slide images as primary diagnosis. The image storage 102 also stores a browsing history of a virtual slide image by the SNS client 20.

A comment-seeker posts a virtual slide image via the SNS client 20. The image control section 101 receives the virtual slide image, and stores the virtual slide image in the image storage 102. Further, the image control section 101 provides a virtual slide image, of which comment is being wanted, in response to a request by a user via the SNS client 20. The user browses the virtual slide image to post a double check or a second opinion.

The SNS information storage 104 stores SNS user information, and information other than a virtual slide image in primary diagnosis by a comment-seeker. Further, the SNS information storage 104 stores comments from applicants, who submit a comment being wanted, a friend list (described later), a blacklist (described later), automatically-calculated reliability scores of comments, and the like.

The SNS control section 103 manages the pathologist-dedicated SNS system 100 based on SNS information stored in the SNS information storage 104. Specifically, the SNS control section 103 stores a primary diagnosis by a comment-seeker, which is posted by the SNS client 20, in the SNS information storage 104, to thereby manage the pathologist-dedicated SNS system 100. Similarly, the SNS control section 103 stores a comment as a double check or a second opinion, which is posted by the SNS client 20, to thereby manage the pathologist-dedicated SNS system 100. The SNS control section 103 operates in cooperation with the image control section 101. As a result, both the SNS service and a virtual slide image are provided to a user seamlessly.

The network connecting device 18 of the SNS server 10 provides functions to the image control section 101 and the SNS control section 103 such that the image control section 101 and the SNS control section 103 communicate with the SNS client 20.

[Functional Block of SNS Client 20]

Figure 4:
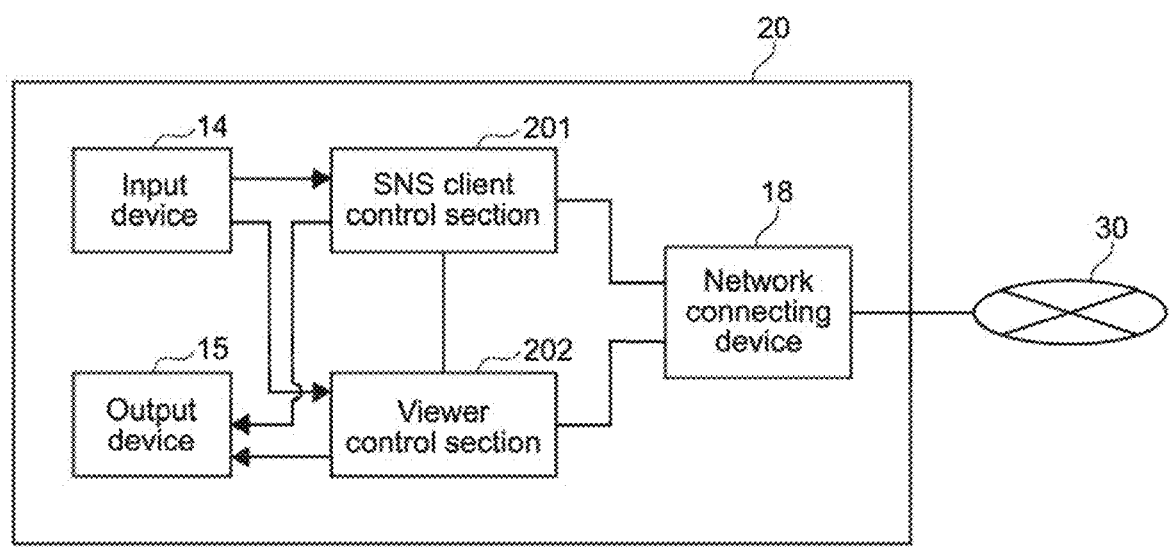
FIG. 4 is a diagram showing the functional blocks of an SNS client 20.

FIG. 4 is a diagram showing the functional blocks of the SNS client 20. The SNS client 20 includes the SNS client control section 201, the viewer control section 202, the above-mentioned input device 14, the above-mentioned output device 15, and the above-mentioned network connecting device 18.

The SNS client control section 201 provide an SNS window to the above-mentioned seeker or applicant via the output device 15. Further, the SNS client control section 201 receives a primary diagnosis by a seeker and a comment by an applicant via the input device 14 and via the SNS window. The provided SNS window is based on SNS information, which is obtained from the SNS information storage 104 of the SNS server 10 via the network 30. Further, the received seeker's primary diagnosis and applicant's comment are stored in the SNS information storage 104 of the SNS server 10 via the network 30.

The viewer control section 202 provides a viewer screen to a seeker or an applicant via the output device 15. The seeker or the applicant browses a virtual slide image on the viewer screen. The viewer control section 202 obtains a virtual slide image, which is provided to a seeker or an applicant by a viewer, from the image storage 102 of the SNS server 10. The viewer control section 202 receives operation instructions from a seeker or an applicant via the input device 14. Examples of the operation include zooming in/out, moving, and rotating a virtual slide image. The viewer control section 202 executes the instructed operation.

Further, the viewer control section 202 records a history of display operation as a display history. The display operation is input to browse a virtual slide image by a seeker or an applicant. Further, the viewer control section 202 records a motion picture of the process that an applicant browses a virtual slide image, and the voice of the applicant, together. The recorded display history and the recorded motion picture are stored in the SNS information storage 104 of the SNS server 10 via the network 30.

The network connecting device 18 of the SNS client 20 provides functions to the SNS client control section 201 and the viewer control section 202 such that the SNS client control section 201 and the viewer control section 202 communicate with the SNS server 10.

[Viewer Screen]

Figure 5:
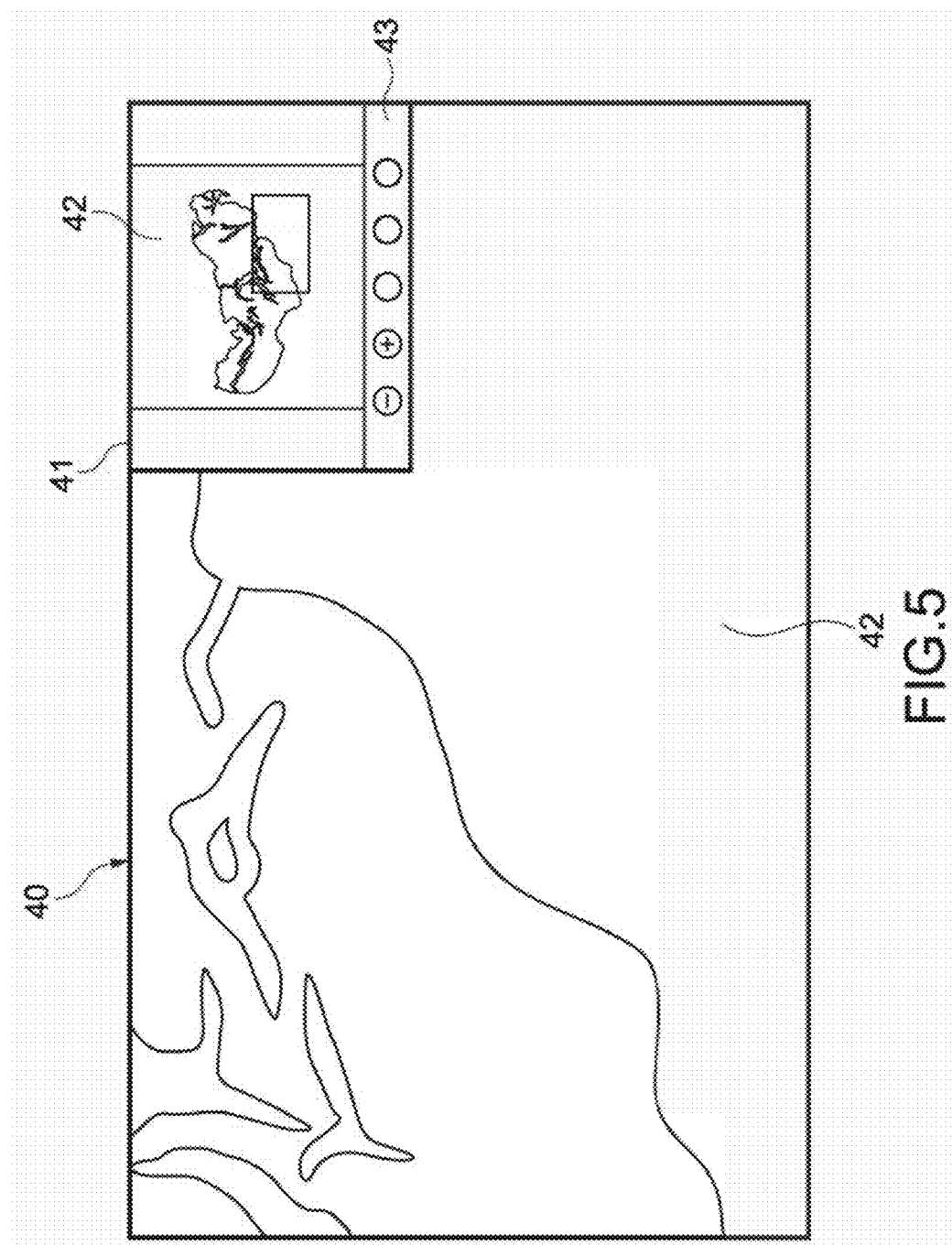
FIG. 5 is a diagram showing an example of a viewer screen.

Next, the above-mentioned viewer screen will be described. FIG. 5 is a diagram showing an example of the viewer screen.

A viewer window 40 includes an image control GUI 41. The image control GUI 41 receives instructions for controlling the image displayed on the image control GUI 41, by a user. The image control GUI 41 includes a thumbnail map 42 and a thumbnail map control GUI 43. The thumbnail map 42 includes a reduced image of the whole virtual slide image, and a frame. The frame equivalently shows the area of the image, which is displayed on the viewer window 40, in the thumbnail map 42. In response to an instruction by a user, the frame may be moved in an arbitrary direction and by an arbitrary distance, on the thumbnail map 42.

The viewer control section 202 calculates location information of the image, which is displayed on the viewer window 40, based on operation information on movement of the frame. Meanwhile, the thumbnail map control GUI 43 includes GUI elements such as a plurality of buttons. The GUI element receives instructions for controlling an image, by a user. Examples of the instructions include moving, changing a zoom factor, and rotating a display area of an image, which is displayed on the viewer window 40. Note that a user may drag a mouse or the like to thereby move a frame in the thumbnail map 42.

Note that the viewer screen may display a display history of virtual slides browsed by an applicant, and may reproduce a recorded motion picture and a recorded sound of the browsing process (not shown).

[Display History]

Figure 6:
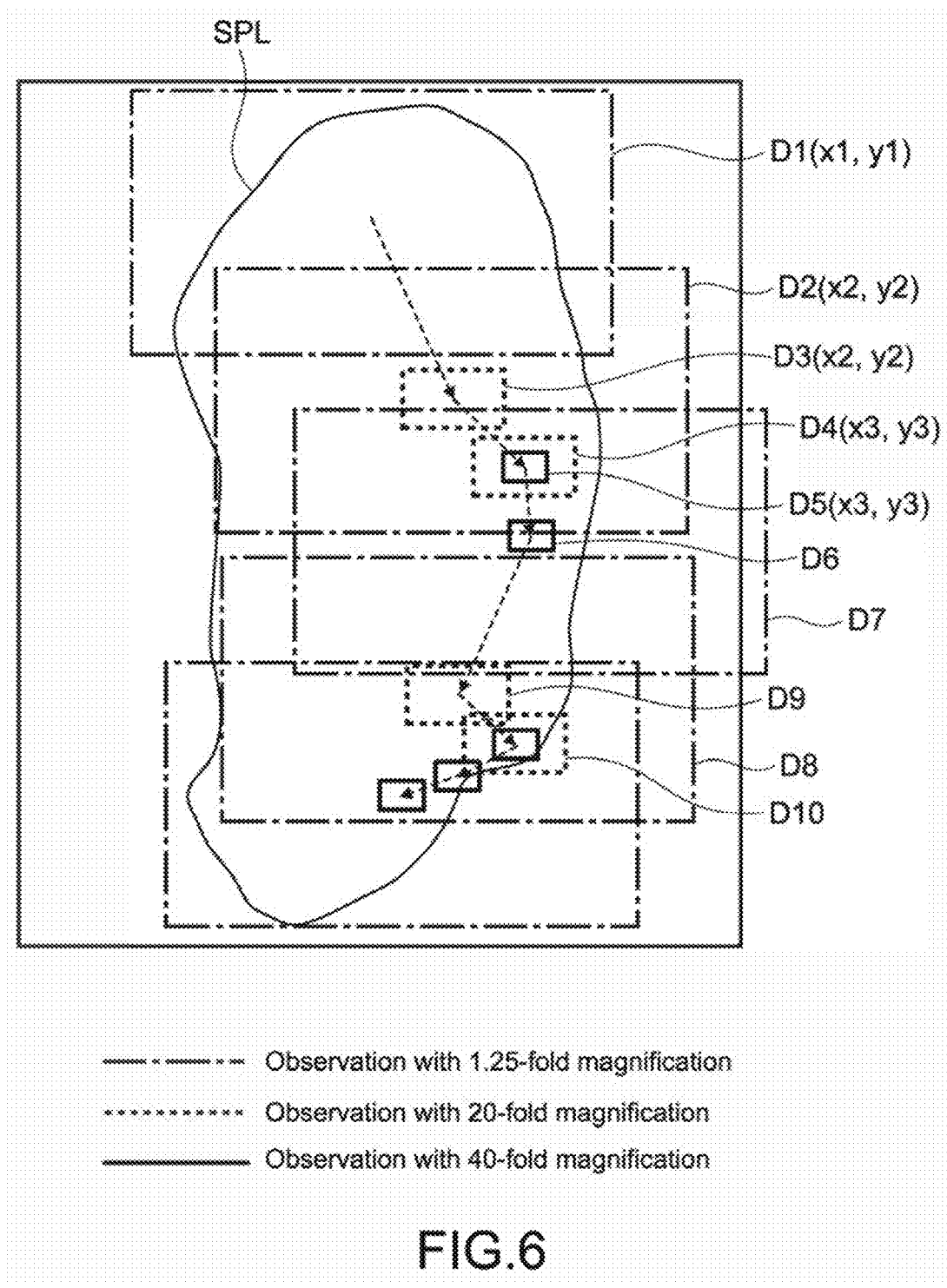
FIG. 6 is a diagram showing a process that a seeker or an applicant browses a sample SPL displayed on a viewer window 40, the picture of the sample SPL being took as a virtual slide image.
Figure 7:
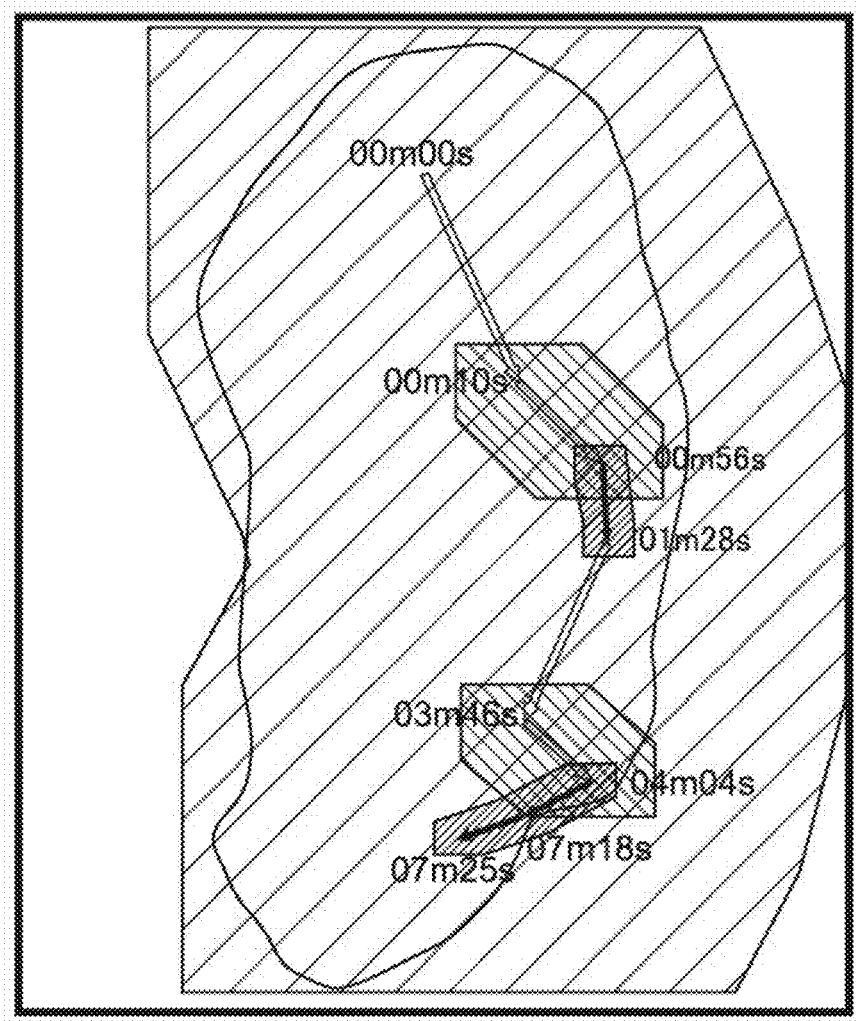
FIG. 7 is a diagram showing an example of recording a display history of browsing process.

Next, the above-mentioned display history will be described. FIG. 6 is a diagram showing a process that a seeker or an applicant browses a sample SPL displayed on the viewer window 40. The picture of the sample SPL is took as a virtual slide image. FIG. 7 is a diagram showing an example in which the browsing process is recorded as a display history.

First, with reference to FIG. 6, operation by a seeker or an applicant (here, referred to as "visitor") and how a virtual slide image is displayed will be described. The virtual slide image is an obtained image of the sample SPL.

Operated by a visitor, the upper area D1 of the sample SPL, as a partial image, is displayed with 1.25-fold observation magnification in the viewer window 40. Note that the central coordinate of the display area D1 is (x1,y1).

Next, the visitor changes the display area of the partial image from D1 to D2. The central coordinate of the display area D2 of the partial image is (x2,y2).

Next, operated by the visitor, the observation magnification is rescaled from 1.25-fold to 20-fold, and the display area D3 of the partial image is thus displayed. At this time, the central coordinate of the partial image is not changed, and is still (x2,y2).

Next, operated by the visitor, the display area D3 of the partial image is moved to the display area D4. The central coordinate of the partial image is (x3,y3).

Next, operated by the visitor, the observation magnification is rescaled from 20-fold to 40-fold, and the display area D5 of the partial image is thus displayed. At this time, the central coordinate of the partial image is not changed, and is still (x3,y3).

Hereinafter, the visitor browses the partial image in the same manner. In this manner, when a visitor is browsing a virtual slide image, the viewer control section 202 establishes correspondence between central coordinate information on each output partial image and information on its observation magnification, for each output partial image. The viewer control section 202 stores information on the correspondence as a display history of partial images, in the RAM 13 or in the storage device 16 of the SNS client 20.

If a visitor is an applicant, as described above, the viewer control section 202 records a motion picture of the browsing process and the voice of the applicant together, in the RAM 13 or in the storage device 16 of the SNS client 20.

Next, with reference to FIG. 7, an example of recording a display history in the above-mentioned browsing process will be described.

There are three kinds of hatched areas. The coarsest hatched area indicates an area displayed with the 1.25-fold observation magnification. The second coarsest hatched area indicates an area displayed with the 20-fold observation magnification. The finest hatched area indicates an area displayed with the 40-fold observation magnification.

Further, the white arrow indicates a path of a central coordinate when a display area moves with 1.25-fold observation magnification. The gray arrow indicates a path of a central coordinate when a display area moves with 20-fold observation magnification. The black arrow indicates a path of a central coordinate when a display area moves with 40-fold observation magnification.

Further, the time stamp recorded in the vicinity of each arrow indicates elapsed time after the display area D1 is displayed, operated by a visitor.

The display history and the motion picture, which are recorded in the RAM 13 or in the storage device 16 of the SNS client 20, are finally stored in the SNS information storage 104 of the SNS server 10 via the SNS client control section 201 and via the SNS control section 103 of the SNS server 10. Note that the display history and the motion picture may be stored in the SNS information storage 104 when, for example, a visitor finishes using a viewer screen.

[Flow of Use of Pathologist-Dedicated SNS System 100]

Figure 8:
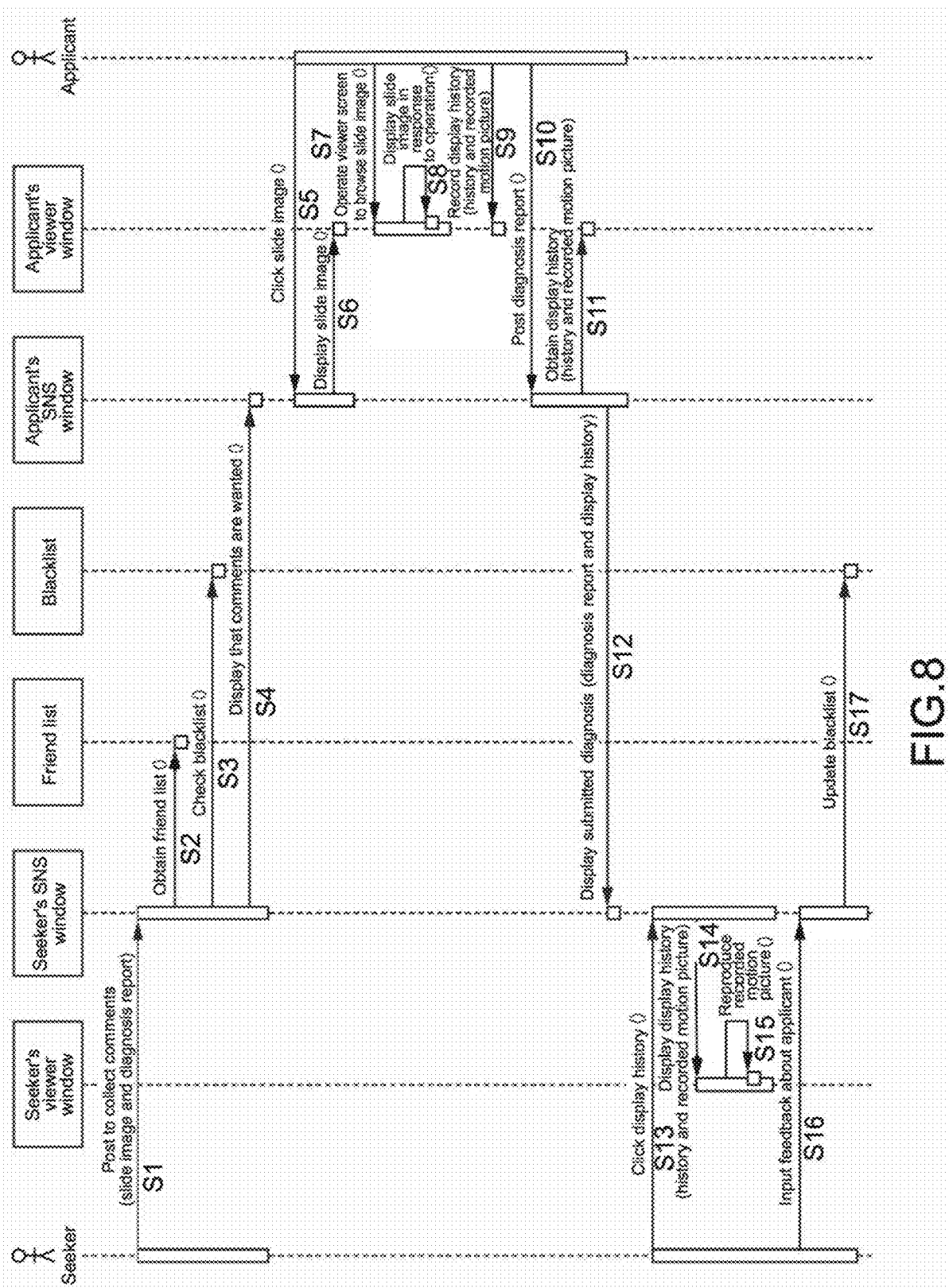
FIG. 8 is a sequential diagram showing a flow when the pathologist-dedicated SNS system is used.

Next, with reference to FIG. 8, the entire flow of use of the pathologist-dedicated SNS system 100 will be described. FIG. 8 is a sequential diagram showing the flow of use of the SNS system.

First, a seeker logs in to his SNS window. The seeker posts virtual slide images and a diagnosis report of his primary diagnosis on the pathologist-dedicated SNS system 100. The seeker instructs the pathologist-dedicated SNS system 100 to collect comments (S1).

The SNS client control section 201 of the SNS client 20 stores the posted virtual slide images in the image storage 102 via the network 30 and via the image control section 101 of the SNS server 10. Further, the SNS client control section 201 of the SNS client 20 stores the posted diagnosis report of the primary diagnosis in the SNS information storage 104 via the network 30 and via the SNS control section 103 of the SNS server 10.

Next, the SNS client control section 201 of the SNS client 20 obtains a friend list (S2). The friend list is stored in the SNS information storage 104 of the SNS server 10.

Next, the SNS client control section 201 of the SNS client 20 checks a blacklist (S3). The blacklist is stored in the SNS information storage 104 of the SNS server 10.

There may be the following two methods, for example, as methods of collecting comments. One method is to make the posting available to all the people registered in the friend list except for people registered in the blacklist, and to seek applicants. The other method is to analyze a social graph of people registered in the friend list, to determine that people having more links have higher reliability, to sort the friend list in the order of reliability, to display the sorted friend list, and to select applicant candidates from the sorted friend list, by a seeker.

Next, the SNS control section 103 of the SNS server 10 displays that comments are wanted on SNS windows of SNS users (applicant candidates) (S4). The SNS users (applicant candidates) are determined based on the friend list and the blacklist.

FIG. 9 shows an example of an article for collecting comments. The article is displayed on the SNS window of each applicant candidate. A message "people, who double check the following pathological diagnosis, are wanted" is displayed on the upper left side of the window. The name of a pathologist, who wants comments, is displayed on the upper right side of the window. Thumbnails VS of the posted virtual slides are displayed on the left side of the window. Further, histopathological diagnosis DG is displayed on the right middle portion of the window. Observation OB is displayed on the lower right portion of the window.

Next, the applicant, who has logged in to the pathologist-dedicated SNS system 100, reads the histopathological diagnosis DG and the observation OB of the article for collecting comments, which is displayed on his SNS window. The applicant clicks a thumbnail VS of a virtual slide image (S5).

Next, the SNS client control section 201 of the SNS client 20 provides an instruction to the viewer control section 202, in order to display a virtual slide image corresponding to the clicked thumbnail VS. The SNS client control section 201 launches the viewer screen. The SNS client control section 201 starts submitting process (S6).

The virtual slide image corresponding to the clicked thumbnail VS is displayed on the launched viewer screen.

Next, the applicant candidate browses a virtual slide image by using the viewer screen (S7).

Next, the viewer control section 202 of the SNS client 20 receives an instruction of image display operation from the applicant candidate. The viewer control section 202 zooms in/out, moves, and rotates the virtual slide image (S8).

The viewer control section 202 of the SNS client 20 records display history of the operation of S8, the image display operation, and voice of the applicant during the operation, in the RAM 13 or in the storage device 16 (S9).

Note that an applicant candidate is capable of setting a plurality of flags at positions, to which the applicant candidate wishes to refer in a submitted comment, when the applicant candidate is browsing a virtual slide image. A seeker is capable of directly accessing partial images (hereinafter, referred to as scenes) on which flags are set, by using the flags as keys.

Next, an applicant candidate (hereinafter, referred to as applicant) posts a diagnosis report as a submitted comment via the SNS window, based on the result of browsing the virtual slide image (S10).

Figure 10:
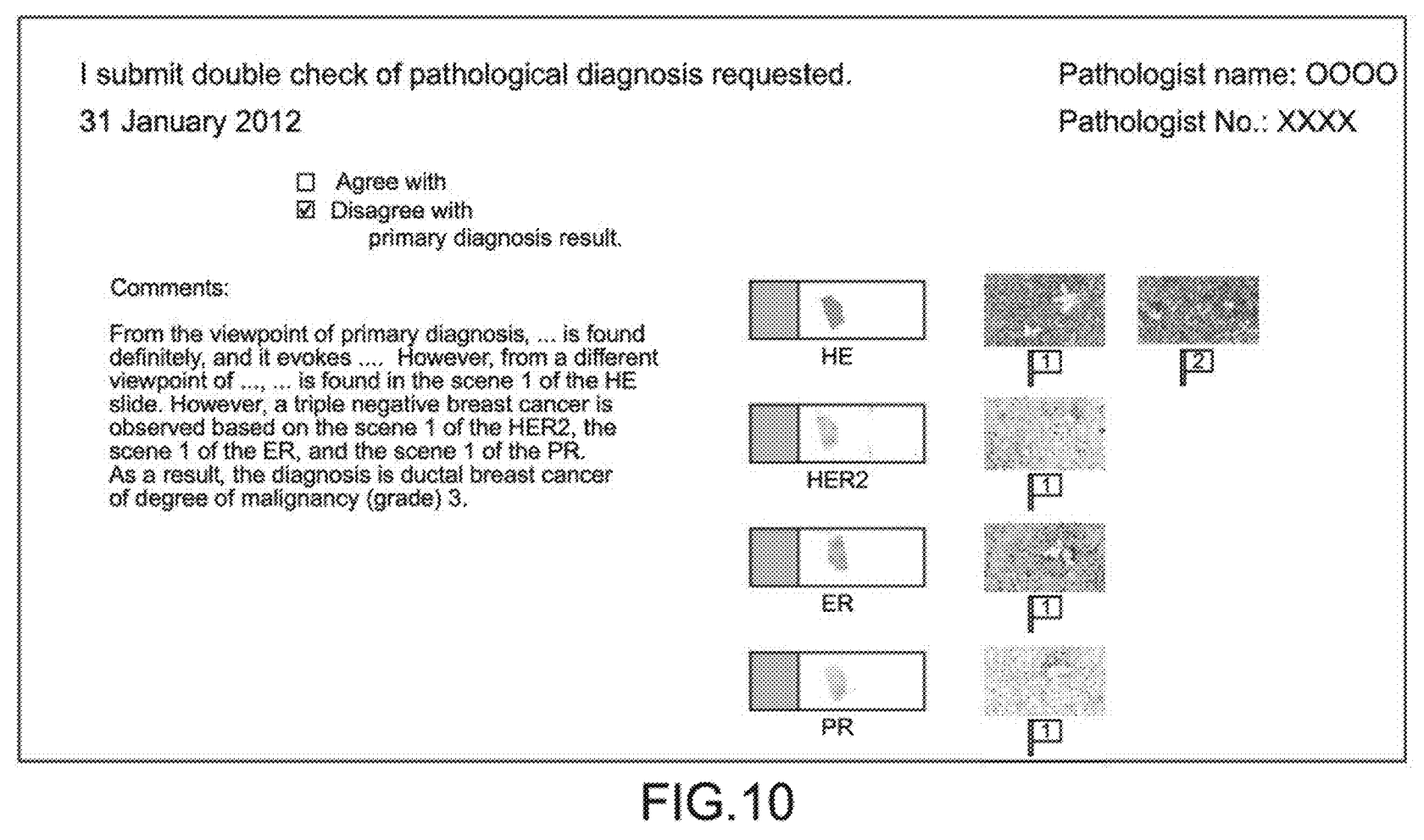

FIG. 10 is a diagram showing an example of a diagnosis report window (submission window) posted by an applicant. A message "I submit double check of pathological diagnosis requested" is displayed on the upper left side of the submission window. Options whether an applicant agrees with the primary diagnosis result or not are displayed below the message.

An option, which shows whether an applicant agrees with primary diagnosis or not, is explicitly checked. As a result, a seeker is capable of easily filtering a plurality of submitted comments, displaying only comments by applicants, who disagree with the primary diagnosis, and the like.

The name of a pathologist, i.e., an applicant, is displayed on the upper right side of the submission window. The thumbnail images HE, HER2, ER, and PR of four virtual slides are shown below the pathologist's name. A list of thumbnail images of scenes, on which flags are set, in each virtual slide image is displayed on the right side of each thumbnail image. For example, it is understood that an applicant has set flags on two positions in the virtual slide HE.

When a thumbnail image of a scene is clicked, a viewer screen is started. The scene is displayed in the viewer window 40 of the viewer screen. Note that the virtual slide name, the central coordinate when displayed, the observation magnification, and the rotation angle, as scene information, are stored. Correspondence between the scene information and a thumbnail image of each scene is established.

The posted diagnosis report, the above-mentioned scene information, and the like are stored in the SNS information storage 104 of the SNS server 10.

The sequential diagram will be described again.

An applicant posts a diagnosis report on the pathologist-dedicated SNS system 100. Next, the SNS client control section 201 obtains the display history of an applicant, who browsed a virtual slide image, and the recorded motion picture, via the viewer control section 202. Then, the SNS client control section 201 stores the display history and the recorded motion picture in the SNS information storage 104 via the network 30 and via the SNS control section 103 of the SNS server 10 (S11).

Next, the SNS control section 103 of the SNS server 10 displays icons, an article caption, and the like, on the SNS window of a seeker (S12). As a result, a seeker is capable of accessing the posted diagnosis report, the recorded display history, and the recorded motion picture.

Further, the SNS control section 103 of the SNS server 10 automatically generates a reliability score of the submitted diagnosis report. How to automatically generate a reliability score will be described later.

Next, a seeker logs in to his SNS window. The seeker clicks an icon indicating a display history (S13). The icon is displayed on his SNS window by the SNS client control section 201 of the SNS client 20.

At this time, the seeker is capable of watching a displayed list of comments submitted by a plurality of applicants. A reliability score of a diagnosis report by each applicant is displayed in the list. It is possible to sort diagnosis reports in the order of reliability, and to check what is written in each diagnosis report in the order of reliability.

In S13, the seeker clicks an icon indicating a display history. Next, the SNS client control section 201 of the SNS client 20 causes the viewer control section 202 to launch a viewer screen, in order to display the display history. The viewer control section 202 displays the display history (S14).

When a seeker clicks a thumbnail image indicating a scene, the viewer screen is launched too, and the corresponding scene is displayed.

Next, a seeker instructs reproduction of the recorded motion picture on the viewer screen. Then, the recorded motion picture is reproduced (S15).

A seeker watches the browsing history of an applicant, who wrote a diagnosis report as a double check or a second opinion, and the recorded motion picture. As a result, it is possible to repeat the display operation by the applicant, as if the seeker is by the side of the applicant and is watching his browsing behavior. Because of this, it is possible to improve reliability of the diagnosis report.

Next, the seeker input feedback about the applicant in his SNS window (S16). The feedback is input as the result of watching the diagnosis report, the scene image, the display history, and the recorded motion picture.

A seeker determines that an applicant has no reliability, as the result of watching the display history and the recorded motion picture. The seeker marks the applicant, and then the applicant is on a blacklist. As a result, a notice of collecting comments may not be supplied to the applicant from the next time.

The SNS client 20 receives the feedback about the applicant. Next, the SNS client control section 201 of the SNS client 20 updates the blacklist, which is stored in the SNS information storage 104, via the SNS control section 103 of the SNS server 10 (S17).

The entire flow of use of the pathologist-dedicated SNS system 100 has been described above.

[Automatic Generation of Reliability Score]

Next, how the SNS control section 103 of the SNS server 10 automatically generates a reliability score of a posted diagnosis report will be described.

Figure 11:
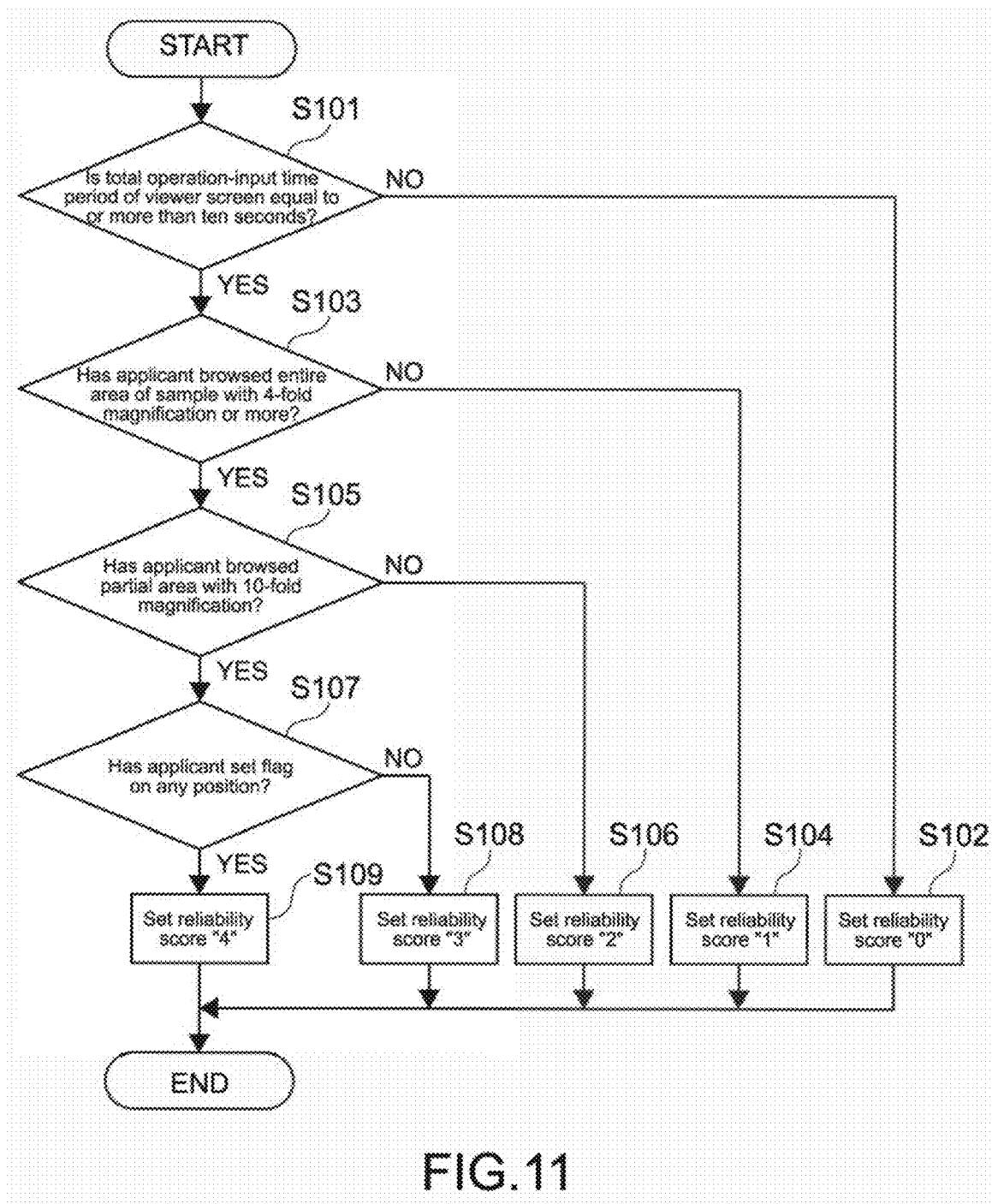
FIG. 11 is a flowchart showing a method of generating a reliability score of a diagnosis report posted by an applicant.

FIG. 11 is a flowchart showing how to generate a reliability score of a diagnosis report posted by an applicant.

First, the SNS control section 103 of the SNS server 10 determines if an operation time period of a viewer screen by an applicant is equal to or more than a predetermined time period or not, based on the display history of the applicant (Step S101). Here, in this example, the predetermined time period is, for example, ten seconds (Step S101).

If the total operation time period of a viewer screen is equal to or more than ten seconds, the next S103 is performed. If the total operation time period of a viewer screen is less than ten seconds, a reliability score "0" is set in S102, and the process is finished.

S101 indicates the following facts. The SNS control section 103 (second information obtaining section) obtains, as a display history (browsing history), information at least including information on a browsing time period of a virtual slide image (pathological image). The SNS control section 103 (reliability score generating section) generates a reliability score of the obtained opinion, based on at least the obtained browsing time period.

In S101, it is determined that the total operation time period of a viewer screen is equal to or more than ten seconds. In this case, next, the SNS control section 103 determines if the applicant has browsed the entire area of the sample SPL with predetermined first observation magnification or more, or not, based on the display history of the applicant (Step S103). Here, let's say the predetermined first observation magnification is 4-fold.

If the applicant has browsed the entire area of the sample SPL with 4-fold observation magnification or more, the next S105 is performed. If the applicant has not browsed the entire area of the sample SPL with 4-fold observation magnification or more, a reliability score "1" is set in S104, and the process is finished.

In S103, it is determined that the entire area of the sample SPL has been browsed with 4-fold observation magnification or more. In this case, next, the SNS control section 103 determines if the applicant has browsed a partial area of the sample SPL with predetermined second observation magnification or more, or not, based on the display history of the applicant (Step S105). The predetermined second observation magnification is larger than the first observation magnification. The predetermined second observation magnification is, for example, 10-fold.

If a partial area of the sample SPL has been browsed with 10-fold observation magnification or more, the next S107 is performed. If a partial area of the sample SPL has not been browsed with 10-fold observation magnification or more, a reliability score "2" is set in S106, and the process is finished.

S103 and S105 indicate the following facts. The SNS control section 103 (second information obtaining section) obtains, as a display history (browsing history), information at least including information on observation magnification of a virtual slide image (pathological image). The SNS control section 103 (reliability score generating section) generates a reliability score of the obtained opinion, based on at least the obtained observation magnification. Further, the SNS control section 103 (second information obtaining section) obtains, as a display history (browsing history), information at least including information on a browsed area in a virtual slide image (pathological image). The SNS control section 103 (reliability score generating section) generates a reliability score of the obtained opinion, based on at least the obtained browsed area.

In S105, it is determined that a partial area of the sample SPL has been browsed with 10-fold observation magnification or more. In this case, next, the SNS control section 103 determines if the applicant has set a flag on any scene (Step S107).

If it is determined that the applicant has set a flag on any scene, a reliability score "4" is set in S109, and the process is finished. If it is determined that the applicant has not set a flag on any scene, a reliability score "3" is set in S108, and the process is finished.

S107 indicates the following facts. The SNS control section 103 (second information obtaining section) obtains information on a scene (noteworthy position) in a virtual slide image (pathological image), on which a flag is set. The SNS control section 103 (reliability score generating section) generates a reliability score of the obtained opinion, based on at least the fact that the flag (noteworthy position) is obtained or not.

According to the above-mentioned method, it is possible to automatically generate a score (one of reliability "0" to reliability "4") of reliability of a diagnosis report by an applicant, based on a display history of an applicant.

[About Analysis Tool of Viewer Screen]

Next, an analysis tool will be described. The image control section 101 of the SNS server 10 provides the analysis tool via a viewer screen. The analysis tool is configured to compare display histories of a plurality of applicants with a display history of a seeker himself.

Figure 12:
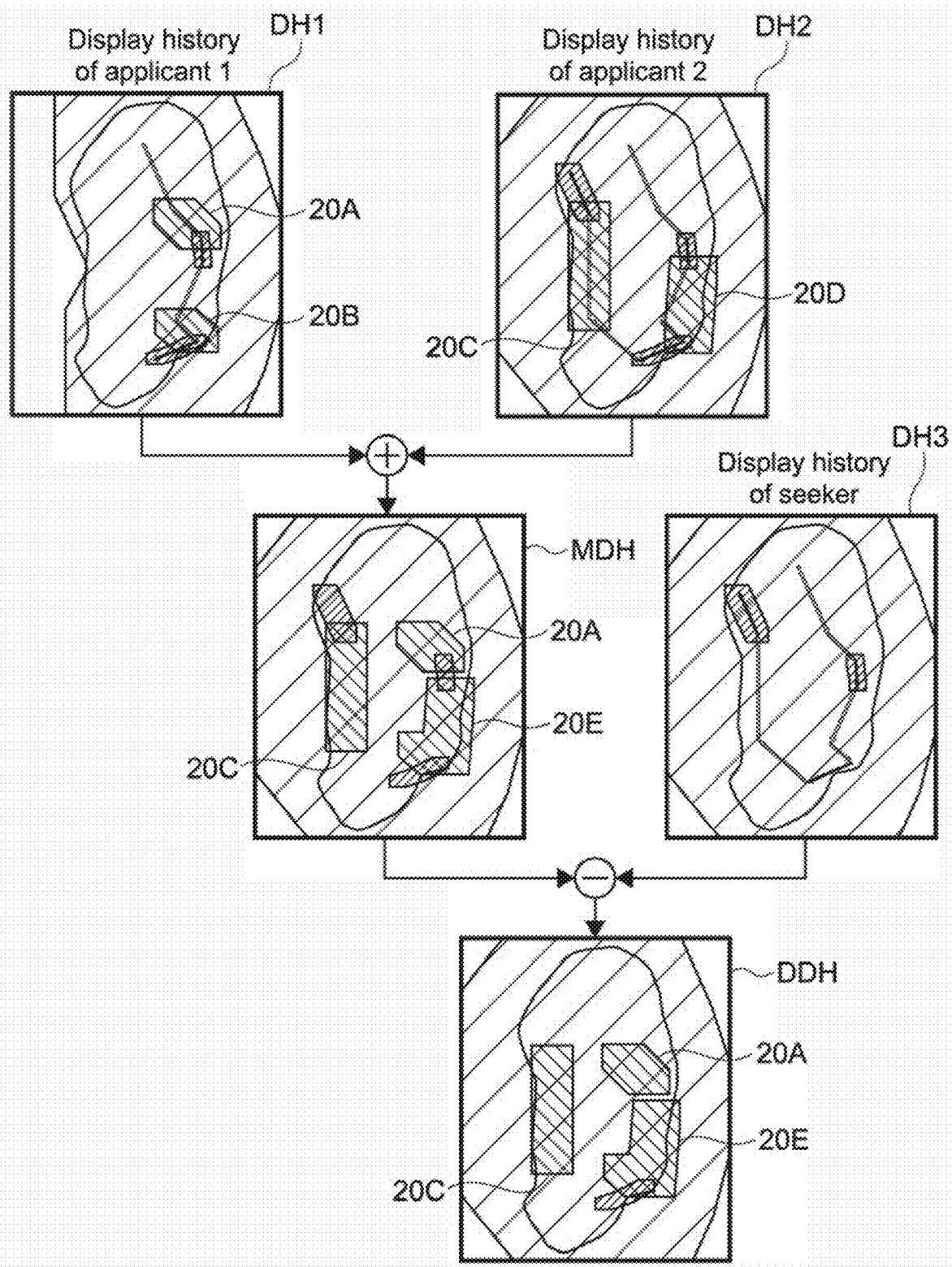
FIG. 12 is a diagram showing a procedure of comparing, by an analysis tool, display histories of a plurality of applicants and a seeker.

FIG. 12 is a diagram showing a procedure for comparing display histories of a plurality of applicants with a display history of a seeker by the analysis tool. First, the image control section 101 obtains an OR (logical add) of a display history DH1 of an applicant 1 and a display history DH2 of an applicant 2. The OR result is referred to as a mixed display history MDH. Here, the display histories of the two applicants are mixed. If there are three or more applicants, an OR of the display histories of all the applicants may be obtained.

For example, let's pay attention to areas, which are displayed with 20-fold observation magnification. The display history DH1 of the applicant 1 includes two areas, which are observed with 20-fold observation magnification, i.e., areas 20A and 20B. The display history DH2 of the applicant 2 includes two areas, which are observed with 20-fold observation magnification, i.e., areas 20C and 20D. The OR result thereof, i.e., the mixed display history MDH, includes the display histories with 20-fold observation magnification, i.e., areas 20A, 20C, and 20E. The area 20E is obtained by mixing the areas 20B and 20D.

Next, the image control section 101 extracts the difference between the mixed display history MDH and a display history DH3 of a seeker himself. The result of extracting the difference is referred to as a difference display history DDH.

For example, let's pay attention to areas, which are displayed with 20-fold observation magnification. The mixed display history MDH includes the three areas 20A, 20C, and 20E. Meanwhile, the display history DH3 of the seeker himself includes no area, which the seeker has observed with 20-fold observation magnification. Therefore, the difference display history DDH shows the areas 20A, 20C, and 20E as the display history difference between the plurality of applicants and the seeker himself.

In this manner, by watching the difference display history DDH, the seeker is capable of finding areas, to which other people have paid attention, and which the seeker has not found.

Note that areas, which are observed by a plurality of applicants, may be overlapped each other in the mixed display history MDH. In this case, a position, in which more areas are overlapped, may be displayed with a darker color. Because of this display, a seeker is capable of knowing how other people have paid attention to the position in the area, which the seeker has not noticed.

[Effects as the Result of Improved Reliability]

As described above, the pathologist-dedicated SNS system of the present technology repeats display operation by an applicant, as if a seeker is by the side of the applicant and is watching the diagnosis behavior. Further, the pathologist-dedicated SNS system of the present technology automatically generates a reliability score. Because of this, it is possible to improve reliability of the diagnosis report. In view of the above, the pathologist-dedicated SNS system of the present technology with higher reliability may be widely used.

[Other Configurations of Present Technology]

Note that the present technology may adopt the following configurations.

(1) An information processing apparatus, comprising:

a first information obtaining section configured to obtain a pathological image and a primary diagnosis result from a first terminal via a network, the first terminal being of a first user being a pathologist, the primary diagnosis result being a diagnosis result about the pathological image by the first user;

an information providing section configured to provide the obtained pathological image and the primary diagnosis result to at least one second terminal via the network, the at least one second terminal being of at least one second user being a pathologist;

a second information obtaining section configured to obtain a browsing history and an opinion of the second user from the second terminal via the network, the browsing history at least including information on a displayed area in the pathological image, the area being displayed based on operation by the second user when the second user observes the pathological image on a display unit of the second terminal, the opinion of the second user being about the primary diagnosis result based on observation of the pathological image by the second user; and a reliability score generating section configured
to estimate the obtained browsing history based on a predetermined condition, and
to generate a reliability score of the obtained opinion.

(2) The information processing apparatus according to (1), wherein the second information obtaining section is configured to obtain, as the browsing history, information at least including information of a browsing time period of the pathological image, and the reliability score generating section is configured to generate a reliability score of the obtained opinion based on at least the obtained browsing time period.

(3) The information processing apparatus according to (1) or (2), wherein the second information obtaining section is configured to obtain, as the browsing history, information at least including information on observation magnification of the pathological image, and the reliability score generating section is configured to generate a reliability score of the obtained opinion based on at least the obtained observation magnification.

(4) The information processing apparatus according to any one of (1) to (3), wherein the second information obtaining section is configured to obtain, as the browsing history, information at least including information on a browsed area in the pathological image, and the reliability score generating section is configured to generate a reliability score of the obtained opinion based on at least the obtained browsed area.

(5) The information processing apparatus according to any one of (1) to (4), wherein the second information obtaining section is configured to obtain information showing a noteworthy position in the pathological image, and the reliability score generating section is configured to generate a reliability score of the obtained opinion based on at least presence/absence of the obtained noteworthy position.

(6) The information processing apparatus according to any one of (1) to (5), further comprising:

a first browsing history obtaining section configured to obtain, as a first browsing history, a browsing history from the first terminal of the first user, the browsing history at least including information on a displayed area in the pathological image, the area being displayed based on operation by the first user when the first user observes the pathological image on a display unit of the first terminal;

a browsing history mixing section configured to mix at least one browsing history of at least one second user to obtain one browsing history being a mixed browsing history, the at least one browsing history being obtained by the second information obtaining section; and a browsing history difference generating section configured to generate difference between the mixed browsing history obtained by the browsing history mixing section and the first browsing history obtained by the first browsing history obtaining section.

(7) An information processing method, comprising:

obtaining, by a first information obtaining section, a pathological image and a primary diagnosis result from a first terminal via a network, the first terminal being of a first user being a pathologist, the primary diagnosis result being a diagnosis result about the pathological image by the first user;

providing, by an information providing section, the obtained pathological image and the primary diagnosis result to at least one second terminal via the network, the at least one second terminal being of at least one second user being a pathologist;

obtaining, by a second information obtaining section, a browsing history and an opinion of the second user from the second terminal via the network, the browsing history at least including information on a displayed area in the pathological image, the area being displayed based on operation by the second user when the second user observes the pathological image on a display unit of the second terminal, the opinion of the second user being about the primary diagnosis result based on observation of the pathological image by the second user; and estimating, by a reliability score generating section, the obtained browsing history based on a predetermined condition, and generating a reliability score of the obtained opinion.

(8) An information processing program, causing a computer to function as:

a first information obtaining section configured to obtain a pathological image and a primary diagnosis result from a first terminal via a network, the first terminal being of a first user being a pathologist, the primary diagnosis result being a diagnosis result about the pathological image by the first user;

an information providing section configured to provide the obtained pathological image and the primary diagnosis result to at least one second terminal via the network, the at least one second terminal being of at least one second user being a pathologist;

a second information obtaining section configured to obtain a browsing history and an opinion of the second user from the second terminal via the network, the browsing history at least including information on a displayed area in the pathological image, the area being displayed based on operation by the second user when the second user observes the pathological image on a display unit of the second terminal, the opinion of the second user being about the primary diagnosis result based on observation of the pathological image by the second user; and
a reliability score generating section configured
to estimate the obtained browsing history based on a predetermined condition, and
to generate a reliability score of the obtained opinion.

It should be understood by those skilled in the art that various modifications, combinations, sub-combinations and alterations may occur depending on design requirements and other factors insofar as they are within the scope of the appended claims or the equivalents thereof.

The invention claimed is:
1. An information processing apparatus, comprising:
circuitry configured to:
obtain, from a first terminal via a network, a pathological image, a first browsing history of the pathological image, and a diagnosis report of the pathological image, wherein
the first terminal is associated with a first user,
the first browsing history includes information of a first observed area in the pathological image,
the first observed area is displayed on a first display screen of the first terminal based on a first user operation, and
the first observed area is displayed for observation of the pathological image;
transmit the pathological image to a second terminal via the network, wherein the second terminal is associated with a second user;
obtain a second browsing history of the pathological image from the second terminal via the network, wherein
the second browsing history includes information of a second observed area in the pathological image, and
the second observed area is displayed on a second display screen of the second terminal based on a second user operation, and
the second observed area is displayed for the observation of the pathological image;
obtain an opinion from the second user based on the observation of the pathological image by the second user, wherein the opinion is for the diagnosis report of the pathological image; and
determine a reliability score of the opinion based on the first browsing history of the pathological image and the second browsing history of the pathological image.

2. The information processing apparatus according to claim 1, wherein the circuitry is further configured to:
obtain time information associated with a browsing time period of the pathological image; and
determine the reliability score of the opinion based on the browsing time period.

3. The information processing apparatus according to claim 1, wherein the circuitry is further configured to:
obtain position information that indicates a specific position in the pathological image; and
determine the reliability score of the opinion based on presence of the specific position.

4. The information processing apparatus according to claim 1, wherein the circuitry is further configured to:
obtain scene information of a scene of the pathological image, wherein
the scene is associated with a flag, and
the flag is set based on a specific user input; and
update the determined reliability score of the opinion based on an availability of the scene information.

5. The information processing apparatus according to claim 1, wherein
the circuitry is further configured to transmit the pathological image and the diagnosis report to at least a specific user, and
at least the specific user is registered in a list for provision of the pathological image and the diagnosis report.

6. A method, comprising:
obtaining, from a first terminal via a network, a pathological image, a first browsing history of the pathological image, and a diagnosis report of the pathological image, wherein
the first terminal is associated with a first user,
the first browsing history includes information of a first observed area in the pathological image,
the first observed area is displayed on a first display screen of the first terminal based on a first user operation, and
the first observed area is displayed for observation of the pathological image;
transmit the pathological image to a second terminal via the network, wherein the second terminal is associated with a second user;
obtain a second browsing history of the pathological image from the second terminal via the network, wherein
the second browsing history includes information of a second observed area in the pathological image, and
the second observed area is displayed on a second display screen of the second terminal based on a second user operation, and
the second observed area is displayed for the observation of the pathological image;
obtain an opinion from the second user based on the observation of the pathological image by the second user, wherein the opinion is for the diagnosis report of the pathological image; and
determining a reliability score of the opinion based on the first browsing history of the pathological image and the second browsing history of the pathological image.

7. A non-transitory computer-readable medium having stored thereon, computer-executable instructions, which when executed by a processor of an information processing apparatus, cause the information processing apparatus to execute operations, the operations comprising:
obtaining, from a first terminal via a network, a pathological image, a first browsing history of the pathological image, and a diagnosis report of the pathological image, wherein
the first terminal is associated with a first user,
the first browsing history includes information of a first observed area in the pathological image,
the first observed area is displayed on a first display screen of the first terminal based on a first user operation, and
the first observed area is displayed for observation of the pathological image;
transmit the pathological image to a second terminal via the network, wherein the second terminal is associated with a second user;
obtain a second browsing history of the pathological image from the second terminal via the network, wherein
the second browsing history includes information of a second observed area in the pathological image, and the second observed area is displayed on a second display screen of the second terminal based on a second user operation, and the second observed area is displayed for the observation of the pathological image;

obtain an opinion from the second user based on the observation of the pathological image by the second user, wherein the opinion is for the diagnosis report of the pathological image; and determining a reliability score of the opinion based on the first browsing history of the pathological image and the second browsing history of the pathological image.

8. The non-transitory computer-readable medium according to claim 7, wherein the operations further comprise:

obtaining time information associated with a browsing time period of the pathological image; and determining the reliability score of the opinion based on the browsing time period.

9. The non-transitory computer-readable medium according to claim 7, wherein the operations further comprise:

obtaining position information indicating a specific position in the pathological image; and determining the reliability score of the opinion based on presence of the specific position.

10. The non-transitory computer-readable medium according to claim 7, wherein the operations further comprise:

obtaining scene information of a scene of the pathological image, wherein
the scene is associated with a flag, and
the flag is set based on a specific user input; and updating the determined reliability score of the opinion based on an availability of the scene information.

11. The information processing apparatus according to claim 1, wherein the circuitry is further configured to:

calculate a difference between the first browsing history of the pathological image and the second browsing history of the pathological image;

determine the reliability score of the opinion based on the calculated difference; and output the reliability score to a display screen.

12. The information processing apparatus according to claim 11, wherein the circuitry is further configured to add the second user to a blacklist.

* * * * *